(12) United States Patent
Roberts et al.

(10) Patent No.: US 6,844,368 B1
(45) Date of Patent: Jan. 18, 2005

(54) COMPOUNDS USEFUL IN PAIN MANAGEMENT

(76) Inventors: Edward Roberts, Höhenweg 12, 4112 Flüh (CH); Tiechao Li, 12853 Turnham Dr., Fishers, IN (US) 46038; Dilip Dixit, 72 Jean Brillant, Roxboro, Quebec (CA), H8Y 2S5; Krzysztof Bednarski, 237 Labrie, Laval, Quebec (CA), H7N 5R6; Jean-Francois Lavallée, 297 des Rosiers, Blainville, Quebec (CA), J7C 2Y8; Dick Storer, 215 Oakridge, Baie d'Urfe, Quebec (CA), H9X 2N3; Wuyi Wang, 2297 Frenette, Ville St-Laurent, Quebec (CA), H4R 1M3

( * ) Notice: Subject to any disclaimer, the term of this patent is extended or adjusted under 35 U.S.C. 154(b) by 0 days.

(21) Appl. No.: 09/460,723

(22) Filed: Dec. 14, 1999

Related U.S. Application Data

(60) Provisional application No. 60/113,541, filed on Dec. 22, 1998.

(51) Int. Cl.[7] ............................................. A61K 31/135
(52) U.S. Cl. ........................ 514/657; 514/567; 564/428; 562/452
(58) Field of Search ........................ 562/452; 564/428; 514/567, 657

(56) References Cited

U.S. PATENT DOCUMENTS

| 4,267,373 A | 5/1981 | Hauck et al. |
| 5,545,755 A | 8/1996 | Lin et al. |

FOREIGN PATENT DOCUMENTS

| EP | 378 456 | 7/1990 | ......... C07C/225/20 |
| GB | 1 377 356 | 12/1974 | ........... C07C/91/46 |
| WO | WO 91/09006 | 6/1991 | |
| WO | WO 92/06967 | 4/1992 | ......... C07D/295/02 |
| WO | WO 95/04028 | 2/1995 | |
| WO | WO 97/16422 | 5/1997 | |

OTHER PUBLICATIONS

Budd, "Analgesic Drugs," *International Encyclopedia of Pharmacology and Therapeutics*, N.E. Williams and H. Wilkinson, Eds., Pergammon: (Oxford) 51–63 (1983).
Hirose, et al., "Hydroxytetrahydronaphthalene Derivatives," Abstract No. 43700e, *Chemical Abstracts* 84(7):458 (1976).
Hirose, et al., "Synthesis and Analgesic Activities of Some 2–amino–1, 1–dialkyl–7–methoxy–1,2,3,4–tetrahydronaphthalenes and Related Compounds," STN International File, Caplus, Caplus Acc. No. 1976:542882, Doc. No. 85:142882.
Lord, et al., "Endogenous Opioid Peptides: Multiple Agonists and Receptors," *Nature* 267:495–499 (1977).
Martin, et al., "The Effects of Morphine– and Nalorphine–Like Drugs in the Nondependent and Morphine–Dependent Chronic Spinal Dog," *J. Pharmacol. Exper. Therap.* 197(3):517–532 (1976).
Takeda, et al., "1,1–Dimethyl–2–dimethylamino–7–hydroxy–1,2,3,4–tetrahydronaphthalene," STN International File Caplus, Caplus, Acc. No. 1973:546294, Doc. No. 79:146294.
International Search Report for PCT/SE98/01501.
Tanabe Seiyaku Co. "1,1–Dimethyl–2–dimethylamino–7–hydroxy–1,2,3,4–tetrahydronaphtahalene" & JP, A2, 48057962, Aug. 14, 1973.
Staneva et al. "Parmacological study of 2–aminotetralin derivatives" Farmatsiya (Sofia) 1984, 34(3), p. 15–19.
Christova et al., "Derivatives of 2–amino–1,2,3,4–tetrahydronaphthalene. VII. Aroyl esters" of cis–and trans–2–dimethylamino–3–hydroxy–5,8–dimethoxy. 1,2,3,4–tetrahydronaphthalenes Arch. Pharm., 1982, 315(9), p. 797–801.
Rainova et al., "Neuropharmacological profile of an aminotetralin derivative", Eksp. Med. Morfol., 1977, 16(4), p. 211–216.
Dantchev et al., "Derivatives of 2–amino–1,2,3,4–tetrahydronaphthalene. II. Synthesis and pharmacological investigation of N–substituted trans–2–amino–3–hydroxy–5, 8–dimethoxy–1,2,3,4–tetrahydronaphthalenes", Arch. Pharm., 1977, 310(5), p. 369–379.
English Abstract of FR above , 1973.
English Abstract of GR above , 1984.
English Abstract of IR above , 1977.
Kratowska et al., Acta Pharmaceutica Suecica, vol. 24, no. 4, 1987, p. 145–152.
Hacksell et al., Journal of Medicinal Chemistry 1984, vol. 27, p. 1003–1007.

*Primary Examiner*—Samuel Barts
(74) *Attorney, Agent, or Firm*—Michael A. Sanzo; Fitch, Even, Tabin & Flannery

(57) ABSTRACT

The present invention relates to novel oxo-aminotetralin compounds of the formula (I)

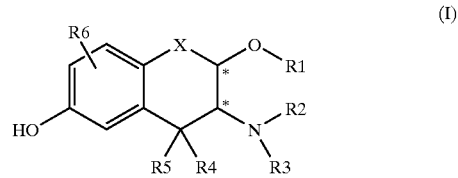

wherein X, $R_1$, $R_2$, $R_3$, $R_4$, $R_5$, and $R_6$ are defined herein.

The compounds of formula (I) are useful in pain management.

32 Claims, No Drawings

COMPOUNDS USEFUL IN PAIN MANAGEMENT

CROSS REFERENCE RELATED APPLICATIONS

The present application claims priority to, and the benefit of, U.S. provisional application 60/113,541, filed on Dec. 22, 1998.

FIELD OF THE INVENTION

The present invention is related to compounds that exhibit analgesic activity and in particular compounds exhibiting analgesia due to their opioid receptor affinity.

BACKGROUND OF THE INVENTION

Many natural alkaloids and related analogs bind to specific opioid receptors and elicit an analgesic response similar to classic narcotic opiates. Many different types of opioid receptors have been shown to coexist in higher animals. For example, see W. Martin et at., *J. Pharmacol. Exp. Ther.* 197, p. 517 (1975); and J. Lord et al., *Nature* (London), 257, p.495 (1977). Three different types of opioid receptors have been identified. The first, δ, shows a differentiating affinity for enkephalin-like peptides. The second, μ, shows enhanced selectivity for morphine and other polycyclic alkaloids. The third, κ exhibits equal affinity for either group of the above ligands and preferential affinity for dynorphin. In general, the μ receptors seem to be more involved with analgesic effects. The δ receptors appear to deal with behavioral effects, although the δ and the κ receptors may also mediate analgesia.

Each opioid receptor, when coupled with an opiate, causes a specific biological response unique to that type of receptor. When an opiate activates more than one receptor, the biological response for each receptor is affected, thereby producing side effects. The less specific and selective an opiate may be, the greater the chance of causing increased side effects by the administration of the opiate.

Opiates can cause serious and potentially fatal side effects. Side effects such as respiratory depression, tolerance, physical dependence capacity, and precipitated withdrawal syndrome are caused by nonspecific interactions with central nervous system receptors. See K. Budd, In *International Encyclopedia of Pharmacology and Therapeutics* N. E. Williams and H. Wilkinson, Eds., Pergammon: (Oxford), 112, p.51 (1983). It is therefore an object of the present invention to provide compounds having analgesic effects but having as few side-effects as possible.

DESCRIPTION OF THE INVENTION

In one aspect, the present invention provides novel oxaaminotetralin compounds which are represented by formula (X):

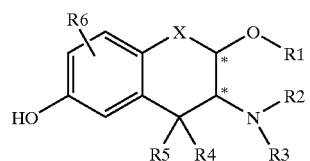

(I)

and pharmaceutically acceptable derivative thereof; wherein;

X is selected from anyone of (i) a bond;

(ii) —$CR_7R_8$— wherein $R_7$ and $R_4$ are independently selected from the group consisting of H, OH, halogen, CN, COOH, $CONH_2$, amino, nitro, SH, $C_{1-6}$ alkyl where one or more of the carbon atoms may optionally be substituted by one or more heteroatoms selected from O, S and N, $C_{2-6}$akenyl where one or more of the carbon atoms may optionally be substituted by one or more heteroatoms selected from O, S and N, $C_{2-6}$alkynyl where one or more of the carbon atoms may optionally be substituted by one or more heteroatoms selected from O, S and N; and $COOR_c$ wherein $R_c$ is $C_{1-6}$alkyl, $C_{2-6}$alkenyl or $C_{2-6}$alkynyl; $R_7$ and $R_8$ can also be connected to form $C_{3-8}$ cycloalkyl, a $C_{3-8}$ cycloalkenyl or a saturated heterocycle of from 3 to 8 atoms;

$R_1$ is selected from the group consisting of H, $C_{1-12}$alkyl where one or more of the carbon atoms may optionally be substituted by one or more heteroatoms selected from O, S and N, $C_{2-12}$alkenyl where one or more of the carbon atoms may optionally be substituted by one or more heteroators selected from O, S and N, $C_{2-12}$alkynyl where one or more of the carbon atoms may optionally be substituted by one or more heteroatoms selected from O, S and N, $C_{2-12}$ aryl, $C_{6-12}$ aralkyl, $C_{6-12}$ aryloxy, $C_{1-12}$ acyl, heteroaryl having from 6 to 12 atoms, and phosphoryl;

$R_2$ and $R_3$ are independently selected from the group consisting of $C_1$ alkyl where one or more of the carbon atoms may optionally be substituted by one or more heteroatoms selected from O, S and N, $C_{2-6}$alkenyl where one or more of the carbon atoms may optionally be substituted by one or more heteroatoms selected from O, S and N, $C_{2-6}$alkynyl where one or more of the carbon atoms may optionally be substituted by one or more heteroatoms selected from O, S and N, $C_{6-12}$ aryl, $C_{6-12}$ aralkyl, heteroaryl having from 6 to 12 atoms, and H; or $R_2$ and $R_3$ may together form a saturated heterocycle of from 3 to 8 atoms;

$R_4$ and $R_5$ are independently selected from the group consisting of $C_{1-6}$ alkyl where one or more of the carbon atoms may optionally be substituted by one or more heteroatoms selected from O, S and N, $C_{2-6}$alkenyl where one or more of the carbon atoms may optionally be substituted by one or more heteroatoms selected from O, S and N, $C_{2-6}$alkynyl where one or more of the carbon atoms may optionally be substituted by one or more heteroatoms selected from O, S and N, and H;

$R_4$ and $R_5$ can also be connected to form $C_{3-8}$ cycloalkyl, a $C_{3-8}$ cycloalkenyl or a saturated heterocycle of from 3 to 8 atoms;

$R_6$ is hydrogen, OH, $C_{1-6}$ alkyl where one or more of the carbon atoms may optionally be substituted by one or more heteroatoms selected from O, S and N, $C_{2-6}$alkenyl where one or more of the carbon atoms may optionally be substituted by one or more heteroatoms selected from O, S and N, $C_{2-6}$alkynyl where one or more of the carbon atoms may optionally be substituted by one or more heteroatoms selected from O, S and N, O—$C_{1-6}$ alkyl where one or more of the carbon atoms may optionally be substituted by one or more heteroatoms selected from O, S and N, O—$C_{2-6}$alkenyl where one or more of the carbon atoms may optionally be substituted by one or more heteroatoms selected from O, S and N, $O_{2-6}$alkynyl where one or more of the carbon atoms may optionally be substituted by one or more heteroatoms selected from O, S and N, halogen, CN, COOH, CONH$_2$, amino, nitro, or SH;
with the provisos that:
1) not both R$_4$ and R$_5$ are H; and
2) at least one of R$_2$ and R$_3$ is H or C$_{1-6}$ alkyl.

The compounds of the present invention are useful in therapy, in particular as analgesics.

In another aspect, there is provided a method of treating pain in a mammal comprising administering to said mammal an analgesic amount of a compound or composition of the present invention.

Still another aspect of the invention is the use of a compound according to formula (I), for the manufacture of a medicament for the treatment of pain.

In another aspect, there is provided pharmaceutical compositions comprising compounds of the present invention and pharmaceutically acceptable carriers, diluents or adjuvants.

X is preferably —CR$_7$R$_8$— wherein R$_7$ and R$_8$ are independently selected from the group consisting of OH, halogen. CN, COOH, CONH$_2$, amino, nitro, SH, C$_{1-6}$ alkyl where one or more of the carbon atoms may optionally be substituted by one or more heteroatoms selected from O, S and N, H, and COOR$_c$ wherein R$_c$ is C$_{1-6}$alkyl; R$_7$ and R$_8$ can also be connected to form a C$_{3-8}$ cycloalkyl.

X is more preferably —CR$_7$R$_8$— wherein R$_7$ and R$_8$ are independently selected from the group consisting of C$_{1-6}$ alkyl, and H.

X is most preferably —CH$_2$—.

R$_1$ is preferably selected from the group consisting of H, C$_{1-12}$alkyl, C$_{6-12}$ aryl, and C$_{6-12}$ aralkyl.

R$_1$ is more preferably selected from the group consisting of C$_{1-6}$alkyl, C$_{6-12}$ aryl, and C$_{6-12}$ aralkyl.

R$_1$ is most preferably C$_{1-6}$alkyl.

R$_1$ can also be

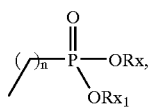

wherein n is an integer between 1 to 5, Rx and Rx$_1$ are independently H, C$_{1-6}$alkyl, C$_{2-6}$alkenyl or C$_{2-6}$alkynyl. More preferably, n is 1 or 2 and Rx and Rx$_1$ are C$_{1-6}$alkyl. Most preferably, Rx and Rx$_1$ are methyl or ethyl.

In an alternative embodiment, R$_1$ is selected from the group consisting of CH$_3$, —(CH$_2$)$_n$—CH$_3$, and —(CH$_2$)$_n$—OCH$_3$ wherein n is an integer selected between 1 and 5 In an alternative preferred embodiment R$_1$ is C$_{6-12}$ aryl or heteroaryl having from 6 to 12 atoms.

In a further preferred embodiment, R$_1$ is selected from the group consisting of

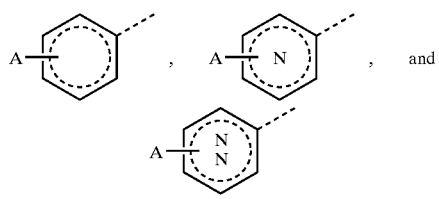

wherein A is selected from the group consisting of C$_{1-6}$ alkyl, C$_{2-6}$alkyl, C$_{2-6}$alkenyl, C$_{2-6}$alkynyl, O—C$_{1-6}$ alkyl, O—C$_{2-6}$alkenyl, OC$_{2-6}$alkynyl, S—C$_{1-6}$alkyl, S—C$_{2-6}$alkenyl, S—C$_{2-6}$alkynyl, N—C$_{1-6}$alkyl, N—C$_{2-6}$alkenyl, N—C$_{2-6}$alkynyl, CF$_3$, fluoro, chloro, bromo, iodo, OH, SH, CN, nitro, amino, aminoamidino, amidino, guanido, COOH, and COOR$_z$ wherein R$_z$ is C$_{1-6}$alkyl, C$_{2-6}$alkenyl or C$_{2-6}$alkynyl.

In an alternative embodiment, R$_1$ is C$_{6-12}$ aralkyl or heteroaryl having from 6 to 12 atoms.

More preferably, R$_1$ is selected from the group consisting of

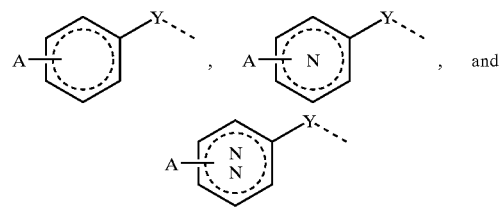

wherein A is selected from the group consisting of C$_{1-6}$ alkyl. C$_{1-6}$alkyl, C$_{2-6}$alkenyl, C$_{2-6}$alkynyl, O—C$_{1-6}$ alkyl, O—C$_{2-6}$alkenyl, O—C$_{2-6}$alkynyl, S—C$_{1-6}$ alkyl, S—C$_{2-6}$ alkenyl, S—C$_{2-6}$alkynyl, N—C$_{1-6}$ alkyl, N—C$_{2-6}$alkenyl, N—C$_{2-6}$alkynyl, CF$_3$, fluoro, chloro, bromo, iodo, OH, SH, CN, nitro, amino, aminoamidino, amidino, guanido, COOH, and COOR$_z$ wherein R$_z$ is C$_{1-6}$alkyl, C$_{2-6}$alkenyl or C$_{2-6}$alkynyl and Y is —(CH$_2$)$_m$— wherein m is an integer selected between 1 and 5.

R$_1$ is preferably

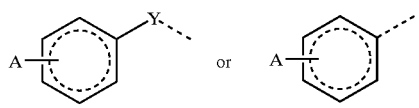

wherein A and Y are as defined above.

A is preferably selected from the group consisting of C$_{1-6}$ alkyl, O—C$_{1-6}$ alkyl, S—C$_{1-6}$ alkyl, OH, nitro, amino, aminoamidino, amidino, guanido, COOH, and COOR$_a$ wherein R$_a$ is C$_{1-6}$alkyl, C$_{2-6}$alkenyl or C$_{2-6}$alkynyl. A is more preferably selected from the group consisting of C$_{1-6}$ alkyl, OH, nitro, amino, aminoamidino, amidino, guanido, and COOH. A is most preferably selected from the group consisting of amidino, guanido, and OH.

R$_2$ and R$_3$ are preferably H.

R$_4$ and R$_5$ are preferably C$_{1-6}$ alkyl substituted by a hydroxyl.

R$_4$ and R$_5$ are preferably C$_{1-6}$ alkyl.

In a further preferred embodiment, R$_4$ and R$_5$ are independently selected from the group consisting of methyl, ethyl, isopropyl, propyl, butyl, and isobutyl.

R$_4$ and R$_5$ are preferably ethyl.

R$_4$ and R$_5$ are preferably methyl.

R$_6$ can be substituted at any position on the aromatic ring. More preferably R$_6$ is adjacent to the carbon bearing the OH. In an alternative embodiment, the present invention provides compounds of the formula (II) or (III)

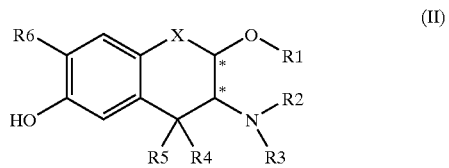

(II)

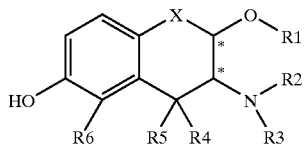

and pharmaceutically acceptable derivative;
wherein each of X, $R_1$, $R_2$, $R_2$, $R_3$, $R_4$, $R_5$, and $R_6$ are defined above.

$R_6$ is preferably, H, methyl, halogen or $OR_b$ wherein $R_b$ is $C_{1-6}$alkyl, $C_{2-6}$alkenyl or $C_{2-6}$alkynyl.

$R_6$ is most preferably H.

The compounds of the present invention contains at least 2 chiral centers which are marked by an asterik (*) on the general formula (1). The compounds of formula (I) thus exist in the form of different geometric (i.e. trans and cis) and optical isomers (i.e. (+) or (−) enantiomers). When there is 2 chiral centers at the position marked by the asteriks, the compounds may be therefore be in the form of cis isomers or trans isomers. Each cis or trans isomers also exists as a (+) and (−) enantiomer. All such isomers, enantiomers and mixtures thereof including racemic mixtures are included within the scope of the invention.

Preferably the compounds of the present invention are in the form of the trans isomers (between the centers marked by an asteriks on the general formula (I)). More preferably the compounds of the present invention are present in the form of trans-(+) enantiomers and trans (−) enantiomers.

Preferred compounds of the invention include:
Trans-7-Amino-6-ethoxy-8,8-diethyl-5,6,7,8-tetrahydro-naphthalen-2-ol (compound#1);
Trans-7-Amino-6-methoxy-8,8-dimethyl-5,6,7,8-tetrahydro-naphthalen-2-ol (compound#2);
Trans-7-Amino-8,8-dimethyl-6-phenoxy-5,6,7,8-tetrahydro-naphthalen-2-ol (compound#3);
Trans-7-Amino-6-isopropoxy-8,8-methyl-5,6,7,8-tetrahydro-naphthalen-2-ol (compound#4);
Trans-7-Amino-8,8-methylpropoxy-5,6,7,8-tetrahydro-naphthalen-2-ol (compound#5);
Trans-7-Amino-8,8-dimethyl-6-(2-phenoxy-ethoxy)-5,6,7,8-tetrahydro-naphthalen-2-ol (compound#6);
Trans-7-Amino-6-ethoxy-8,8-dimethyl-5,6,7,8-tetrahydro-naphthalen-2-ol (compound#7);
Trans-7-Amino-8,8-diethyl-6-(2-methoxy-ethoxy)-5,6,7,8-tetrahydro-naphthalen-2-ol (compound#8);
Trans-7-Amino-8,8-diethyl-6-methoxy-5,6,7,8-tetrahydro-naphthalen-2-ol (compound#9);
Trans-7-Amino-8,8-diethyl-6-(2-hydroxy-ethoxy)-5,6,7,8-tetrahydro-naphthalen-2-ol (compound#10);
Trans-7-Amino-8,8-spiropentanyl-6-methoxy-5,6,7,8-tetrahydro-naphthalen-2-ol (compound#11);
Trans-7-Amino-6-methoxy-8,8-dipropyl-5,6,7,8-tetrahydro-naphthalen-2-ol (compound#12);
Trans-7-Amino-6-ethoxy-8,8-dipropyl-5,6,7,8-tetrahydro-naphthalen-2-ol (compound#13);
Trans-7-Amino-6-(2-phenoxy-ethoxy)-8,8-dipropyl-5,6,7,8-tetrahydro-naphthalen-2-ol (compound#14);
Trans-3-Amino-4,4-diethyl-1,2,3,4-tetrahydro-naphthalene-2,6-diol (compound#15)
(−)Trans-3-Ethoxy-1,1-diethyl-7-hydroxy-1,2,3,4-tetrahydro-naphthalen-2-yl-ammonium chloride (compound #16);
(+)Trans-3-Ethoxy-1,1-diethyl-7-hydroxy-1,2,3,4-tetrahydro-naphthalen-2-yl-ammonium chloride (compound #17);

1,1-diethyl-7-hydroxy-3-trans-3-hydroxy-propoxy)-1,2,3,4-tetrahydro-naphthalen-2-yl-ammonium; chloride (compound#18);
7-Amino-6-(2-amino-ethoxy)-8,8-diethyl-5,6,7,8-tetrahydro-naphthalen-2-ol; BIS-trifluoroacetic acid salt (compound#19);
3-(3-Amino-4,4-diethyl-6-hydroxy-1,2,3,4-tetrahydro-naphthalen-2-yloxy)propionic acid; trifluoroacetic acid salt (compound#20);
and pharmaceutically acceptable derivative thereof; wherein said compound in the form of the (+) enantiomer, the (−) enantiomer and mixture of the (+) and (−) enantiomer including racemic mixture More Preferred compounds of this invention are selected from the group consisting of: compound#1, compound#2, compound#3, compound#4, compound#S, compound#6, compound#7, compound#8, compound#9, compound#12, compound#16, compound#17, compound#18 and compound#19.

Most preferred compounds of the present invention are selected from the group consisting of compound#1, compound#2, compound#5, compound#8, compound#9, compound#16, compound#17, compound#18 and compound#19.

As used in the present application the term "pain" represents an unpleasant sensory and emotional experience associated with actual or potential tissue damage or described in terms of such damage. The term "pain" also includes "acute pain" and chronic pain.

Acute pain is usually immediate and of a short duration. Acute pain can be present further to an injury, short-tern illness, or surgical/medical procedure.

Examples of acute pain include a burn, a fracture, an overused muscle, or pain after surgery. Cancer pain may be long-lasting but acute due to ongoing tissue damage.

Some chronic pain is due to damage or injury to nerve fibers themselves (neuropathic pain).

Chronic pain can result from diseases, such as shingles and diabetes, or from trauma, surgery or amputation (phantom pain). It can also occur without a known injury or disease.

The present invention s directed to the treatment of all type of pain, including acute and chronic pain.

As used in this application, the term "alkyl" represents an unsubstituted or substituted (by a halogen, nitro, aminoamidino, amidino, guanido, $CONH_2$, COOH, O—$C_{1-6}$ alkyl, O—$C_{2-6}$ alkenyl, $OC_{2-6}$ alkynyl, amino, hydroxyl or COOQ, wherein Q is $C_{1-6}$ alkyl, $C_{2-6}$ alkenyl, a $C_{2-6}$ alkynyl) straight chain, branched chain, or cyclic hydrocarbon moiety (e.g. isopropyl, ethyl, flurohexyl or cyclopropyl). The term alkyl is also meant to include alkyls in which one or more hydrogen atoms is replaced by an halogen, more preferably, the halogen is fluoro (e.g., $CF_3$—, or $CF_3CH_2$—).

The term "saturated heterocycle" represents a carbocyclic ring in which one or more of the from 3 to 8 atoms of the ring are elements other than carbon, such as N, S and O;

The term "aryl" represents an aromatic ring having from 6 to 12 carbon atoms, which may be substituted by a $C_{10}$ alkyl, $C_{2-6}$ alkenyl, a $C_{2-6}$ alkynyl, halogen, nitro, aminoamidino, amidino, guanido, $CONH_2$, COOH, $O_{1-6}$ alkyl, O—$C_{2-6}$ alkenyl, O—$C_{2-6}$ alkynyl, amino, hydroxyl or COOQ, wherein Q is $C_{1-6}$ alkyl, $C_{2-6}$ alkenyl, a $C_{2-6}$ alkynyl, such as phenyl and naphthyl.

The term "aralkyl" represents an aryl group attached to the adjacent atom by a $C_{1-6}$alkyl, $C_{1-6}$alkenyl, or $C_{1-6}$alkynyl (e.g., benzyl).

The term "aryloxy-" represents an aryl or aralkyl moiety covalently bonded through an oxygen atom (e.g., phenoxy).

The term "heteroaryl" represents an aromatic ring in which one or more of the from 6 to 12 atoms in the ring are elements other than carbon, such as O, N, and S (e.g. pyridine, isoquinoline, or benzothiophene).

The term "acyl" refers to a radical derived from a carboxylic acid, substituted (by halogen (F, Cl, Br, I), $C_{6-20}$ aryl or $C_{1-6}$ alkyl) or unsubstituted, by replacement of the OH group. Like the acid to which it is related, an acyl radical may be aliphatic or aromatic, substituted (by halogen, $C_{1-5}$ alkoxyalkyl, nitro or OH) or unsubstituted, and whatever the structure of the rest of the molecule may be, the properties of the functional group remain essentially the same (e.g., acetyl, propionyl, isobutanoyl, pivaloyl, hexanoyl, trifluoroacetyl, chloroacetyl, and cyclohexanoyl).

The term "phosphoryl" represents a radical derived from a phosphono moeity in which the hydrogen atom of at least one of the —OH can be replaced by $C_{1-6}$ alkyl $C_{2-6}$alkenyl, $C_{2-6}$alkynyl, $C_{1-6}$heteroalkyl, $C_{6-12}$ aryl, $C_{6-12}$ aralkyl, and $C_{6-12}$ heteroaryl(e.g., diethoxyphosphorylmethyl).

The term "halogen" encompasses chloro, fluoro, bromo and iodo.

When there is a sulfur atom present, the sulfur atom can be at different oxydation level, S, SO, or $SO_2$. All such oxydation level are within the scope of the present invention.

In the present application the following abbreviations are used:
AcOEt ethyl acetate
Boc t-butyloxycarbonyl
DMAP 4-dimethylaminopyridine
DME ethylene glycol dimethylether
DMF dimethylformamide
$Et_2O$ ether
Hex hexane
HPLC high performance liquid chromatography
LAH lithium aluminium hydride
LHMDS lithium bis(trimethylsilyl)amide
NHMDS sodium bis(trimethylsilyl)amide
Ph phenyl
PPTS pyridium p-toluenesulfonate
PTSA p-toluenesulfonic acid
r.t. room temperature
sat. saturated
TFA trifluoroacetic acid
THF tetrahydrofuran
TLC thin layer chromatography In yet another aspect of the invention, there is provided a process for preparing compounds of formula (I). The process is described in scheme I wherein each of X, $R_1$, $R_2$, $R_3$, $R_4$, $R_5$ and $R_6$ are as defined above and P, P1, P2, and P3 are protecting groups.

SCHEME 1

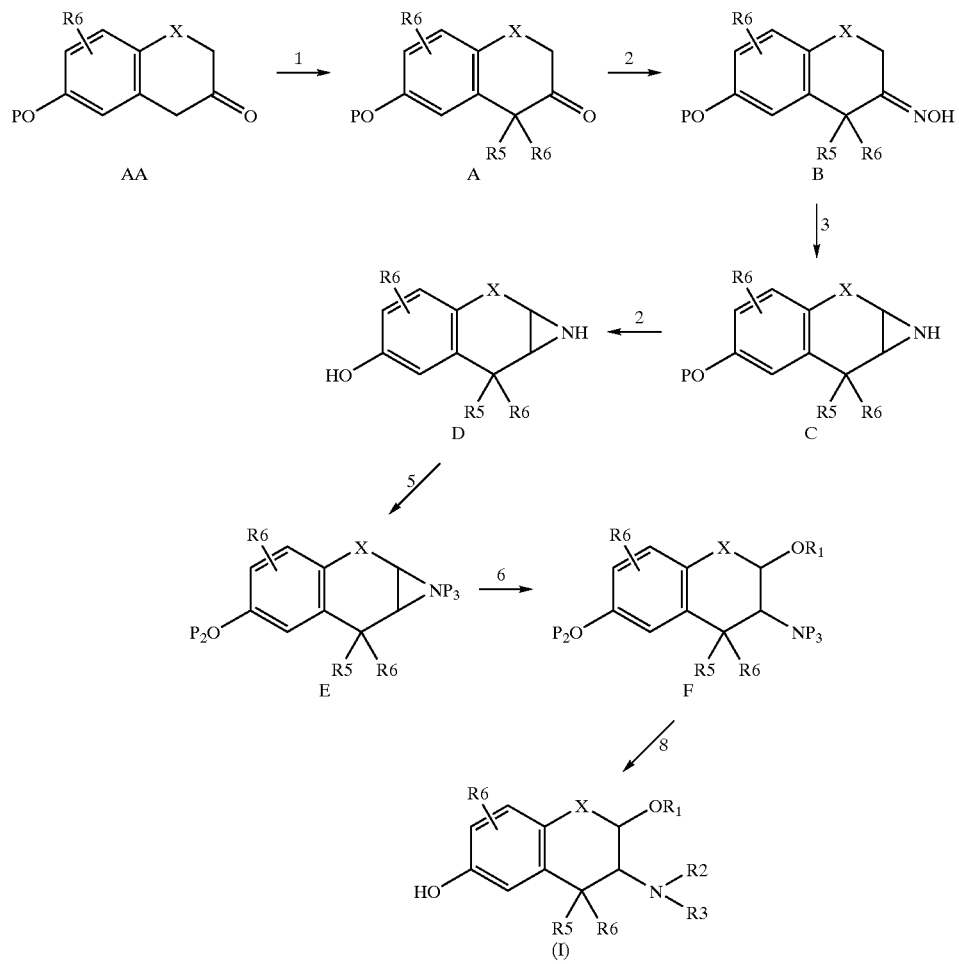

Step 1

The starting ketone AA was dissolved in a suitable solvent such as DMF, acetonitrile, THF, DME and was treated with sodium hydride or any other base such as potassium t-butoxide, sodium bis(trimethylsilyl)amide. The resulting mixture was then treated with ethyl iodide or any other alkyl halide such as methyl iodide, allyl bromide, dilodobutane to produce the compound A.

Step 2

The compound A was dissolved in a suitable solvent such as pyridine, DMF, ethanol and was treated with hydroxylamine hydrochloride or any other hydroxylamine salt such as hydroxylamine sulfate, hydroxylamine bromide to produce the compound B.

Step 3

The compound B was dissolved in a suitable solvent as THF, dioxane, DME, and was treated with LAH or any other reducing agent such as red-Al in presence of diethylamine or any other amine such as methylbutylamine, dipropylamine. The mixture was then heated to 50° C. or at any higher temperature to produce the compound C.

Step 4

The compound C in was dissolved in a suitable solvent as dichloromethane ($CH_2Cl_2$) or in any other solvent such as dichloroethane, and was treated with $BBr_3$ or any other demethylating agent such as $BCl_3$, HBr, to produce the compound D.

Step 5

The amino or hydroxyl groups of the compound D were protected with Boc or with any other protecting, to produce the compound E. Protective groups arm described in *Protective Groups in Organic Synthesis,* 2nd ed., Greene and Wuts, John Wiley & Sons, New York, 1991 which is herein incorporated by reference.

Step 6

The compound E was dissolved in a suitable solvent such as ethanol or in any other alcohol such as methanol, propanol, butanol and was treated with pyridinium p-toluenesulfonate (PPTS) or any other acid or Lewis acid such as HCl, BF3, OEt2. PTSA, to produce the compound F. Alternatively, a non alcoholic solvent can be used in combination with an appropriate amount of an alcohol and a suitable Lewis acid such as ytterbium triflate see for example *Tetrahedron Letters, Vol.* 37, No.43, pp7717–7720, 1996 which is herein-incorporated by reference.

Step 7

The protecting groups of the compound F were removed under appropriate conditions e.g. with TFA or with any other acid such as HCl, PTSA, to produce the compound I.

It will be appreciated that certain substituents require protection during the course of the synthesis and subsequent deprotection. For example, it may be necessary to protect an hydroxyl group by conversion to an alkoxy or an ester and subsequently deprotected. Protective groups for other substituents are described in *Protective Groups in Organic Synthesis,* 2nd ed., Greene and Wuts, John Wiley & Sons, New York, 1991.

In another aspect, there is provided a method of agonizing or activating opioid receptors in a mammal comprising administering to said mammal an opioid receptor agonizing or activating amount of a compound or composition of the invention.

There is also provided a pharmaceutically acceptable compositions comprising compounds of the present invention and derivatives thereof, in combination with pharmaceutically acceptable carriers diluents or adjuvants. By "derivative" is meant any pharmaceutically acceptable-salt, ester, or salt of such ester, of compounds of formula (I) or (II) or any other compound which, upon administration to the recipient, is capable of providing (directly or indirectly) compounds of formula (I) or (II) or an active metabolite or residue thereof.

The present invention also provides pharmaceutical compositions which comprise a pharmaceutically effective amount of a compound of the invention, or pharmaceutically acceptable salts thereof, and preferably, a pharmaceutically acceptable carrier, diluent or adjuvant. The term "pharmaceutically effective amount" is the amount of compound required upon administration to a mammal in order to induce analgesia. Also, the term "opioid receptor agonizing amount" refers to the amount of compound administered to a mammal necessary to bind and/or activate opioid receptors in vivo.

Therapeutic methods of this invention comprise the step of treating patients in a pharmaceutically acceptable manner with those compounds or compositions. Such compositions may be in the form of tablets, capsules, caplets, powders, granules, lozenges, suppositories, reconstitutable powders, or liquid preparations, such as oral or sterile parenteral solutions or suspensions.

In order to obtain consistency of administration, it is preferred that a composition of the invention is in the form of a unit dose. The unit dose presentation forms for oral administration may be tablets and capsules and may contain conventional excipients. For example, binding agents, such as acacia, gelatin, sorbitol, or polyvinylpyrolidone; fillers, such as lactose, sugar, maize-starch, calcium phosphate, sorbitol or glycine; tabletting lubricants such as magnesium stearate; disintegrants, such as starch, polyvinylpyrrolidone, sodium starch glycollate or mnicrocrystalline cellulose; or pharmaceutically acceptable wetting agents such as sodium lauryl sulphate.

The compounds may be administered orally in the form of tablets, capsules, or granules containing suitable excipients such as starch, lactose, white sugar and the like. The compounds may be administered orally in the form of solutions which may contain coloring and/or flavoring agents. The compounds may also be administered sublingually in the form of tracheas or lozenges in which each active ingredient is mixed with sugar or corn syrups, flavoring agents and dyes, and then dehydrated sufficiently to make the mixture suitable for processing into solid form.

The solid oral compositions may be prepared by conventional methods of blending, filling, tableting, or the like. Repeated blending operations may be used to distribute the active agent throughout those compositions employing large quantities of fillers. Such operations are, of course, conventional in the art. The tablets may be coated according to methods well known in nor mal pharmaceutical practice, in particular with an enteric coating.

Liquid oral preparations may be in the form of emulsions, syrups, or elixirs, or may be presented as a dry product for reconstitution with water or other suitable vehicle before use.

Such liquid preparations may or may not contain conventional additives. For example suspending agents, such as sorbitol, syrup, methyl cellulose, gelatin, hydroxyethylcellulose, carboxymethylcellulose, aluminum stearate gel, or hydrogenated edible fats; emulsifying agents, such as sorbitan monooleate or acaci; non-aqueous vehicles (which may include edible oils), such as almond oil, fractionated coconut oil, oily esters selected from the group consisting of glycerine, propylene glycol, ethylene glycol, and ethyl alcohol; preservatives, for instance methyl parahydroxybenzoate, ethyl para-hydroxybenzoate, n-propyl parahydroxybenzoate, or n-butyl parahydroxybenzoate of sorbic acid; and, if desired, conventional flavoring or coloring agents.

The compounds may be injected parenterally; this being intramuscularly, intravenously, or subcutaneously. For parenteral administration, the compound may be used in the form of sterile solutions containing other solutes, for example, sufficient saline or glucose to make the solution isotonic. For parenteral administration, fluid unit dosage forms may be prepared by utilizing the compound and a sterile vehicle, and, depending on the concentration employed, may be either suspended or dissolved in the vehicle. Once in solution, the compound may be injected and filter sterilized before filling a suitable vial or ampoule and subsequently sealing the carrier or storage package. Adjuvants, such as a local anesthetic, a preservative or a buffering agent, may be dissolved in the vehicle prior to use. Stability of the pharmaceutical composition may be enhanced by freezing the composition after filling the vial and removing the water under vacuum, (e.g., freeze drying the composition). Parenteral suspensions may be prepared in substantially the same manner, except that the compound should be suspended in the vehicle rather than being dissolved, and, further, sterilization is not achievable by filtration. The compound may be sterilized, however, by exposing it to ethylene oxide before suspending it in the sterile vehicle. A surfactant or wetting solution may be advantageously included in the composition to facilitate uniform distribution of the compound.

The pharmaceutical compositions of this invention comprise a pharmaceutically effective amount of a compound of this invention and a pharmaceutically acceptable carrier. Typically, they contain from about 0.01% to about 99% by weight, preferably from about 10% to about 60% by weight, of a compound of this invention, depending on which method of administration is employed.

The compounds of the present invention can be administered in combination with one or more further therapeutic agents. Preferably, the one or more further therapeutic agent is selected from the group consisting of nonsteroidal anti-inflammatory drugs (NSAIDs), acetaminophen, narcotics, antidepressants, anticonvulsants, corticosteroid, tramadol, sumatriptan, and capsaicin.

Without limitations, NSAIDs include aspirin (Anacin, Bayer, Bufferin), ibuprofen (Motrin, Advil, Nuprin), naproxen sodium (Aleve) and ketoprofen (Orudis KT)

Without limitations, narcotics include drugs derived from opium (opiates), such as morph ine and codeine, and synthetic narcotics (opioids), such as oxycodone, methadone and meperidine (Deperol).

Without limitations, antidepressants include amitriptyline (Elavil), trazodone (Desyrel) and imipramine (Tofranil) may be used with other analgesics. These drugs are especially useful for neuropathic, head and cancer pain.

Without limitations, anticonvulsants include drugs developed for epilepsy, these drugs, such as phonation (Dilantin) and carbamazepine (Tegretol), can also help control chronic nerve pain.

Tramadol (Ultram) is a synthetic analgesic used primarily for chronic pain, but is also prescribed for acute pain.

Sumatriptan (imitrex) may reduce pain from migraine headache by constricting blood vessels.

Capsaicin (Zostrix), a topical cream made from an extract of red peppers, can help relieve skin sensitivity resulting from shingles. Capsaicin can also be used to treat pain from arthritis, cluster headaches, diabetic neuropathy and pain after mastectomy.

In another aspect of the invention, compounds may be used to identify opioid receptors from non-opioid receptors. For such use, compounds of the invention are radiolabeled e.g. by incorporating $^3$H or $^{14}$C within its structure or by conjugation to $^{125}$I. Such radiolabeled forms can be used directly to identify the presence of opioid receptors and in particular $\mu$ opioid receptors in a receptor population. This can be achieved by incubating membrane preparations with a radiolabeled compound of the invention. The presence and or amount of opioid receptors in the preparation is determined from the difference in membrane bound radioactivity against a control preparation devoid of opioid receptors.

Furthermore, radiolabeled forms of the present compounds can be exploited to screen for more potent opioid ligands, by determining the ability of the test ligand to displace the radiolabeled compound of the present invention.

To further assist in understanding the present invention, the following non-limiting examples are provided. Certain abbreviations are used throughout the examples and can be found in the Aldrich Chemical Company and Bachem catalogues.

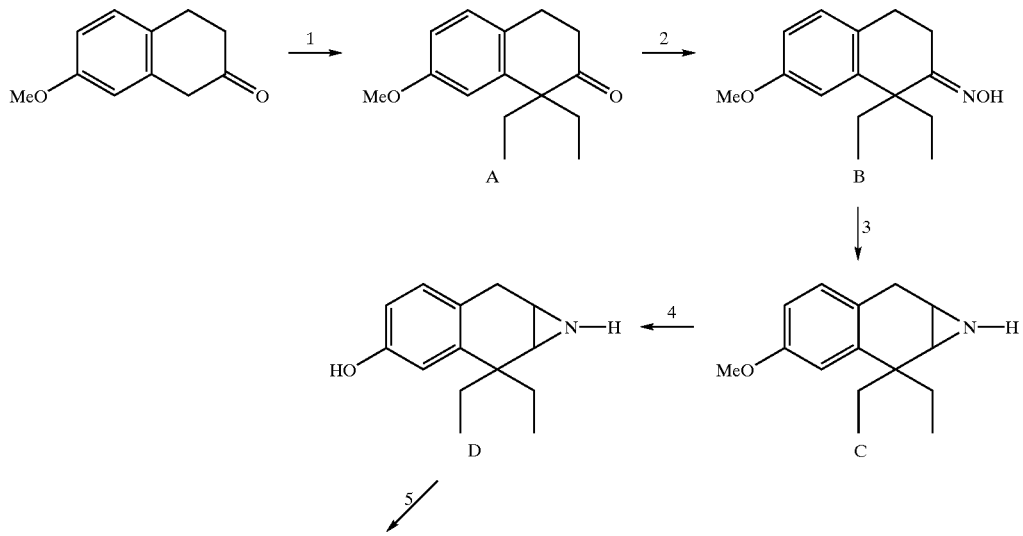

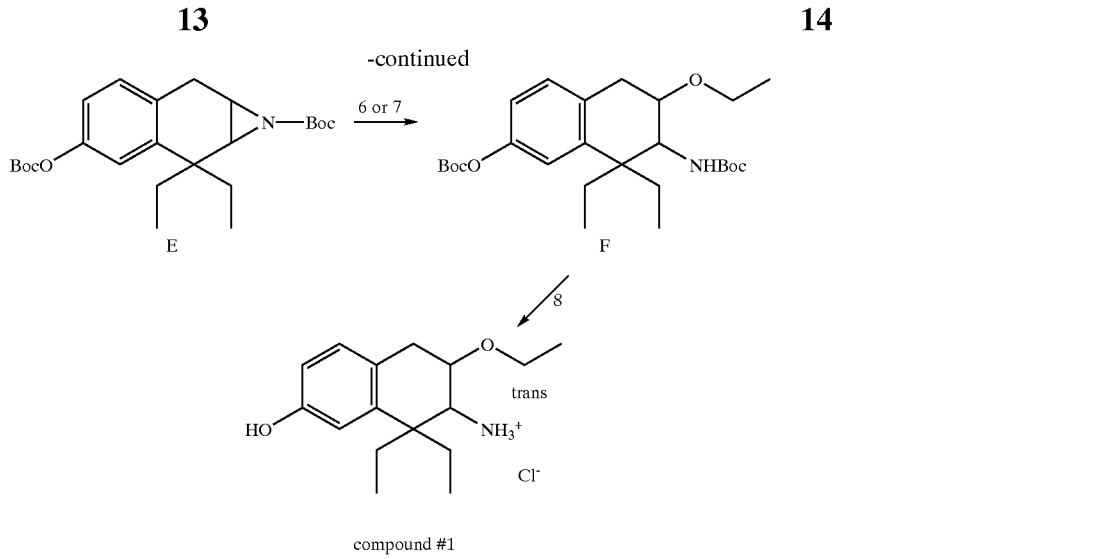

compound #1

EXAMPLE 1

Synthesis of trans-7-Amino-8,9-diethyl-6-methylsulfanyl-5,6,7,8-dihyrdro-naphthalen-2-ol hydrochloride Step 1: 1,1-Diethyl-7-methoxy-3,4-dihydro-1H-naphthalen-2-one (A)

To a solution of 7-methoxy-2-tetralone (4.26 g, 24.18 mmol) in DMF (100 μm) at 0° C. was 1 eq of sodium hydride (60% in oil) (1 g, 41.6 mmol). After 30 minutes, 1.25 eq of iodoethane was added (2.5 mL, 30.2 mmol), then after 30 min, the other equivalent of sodium hydride (1 g), after 30 min the iodoethane was added (2.5 mL, 30.2 mmol). The resulting purpule solution was stirred for 1 h at 0° C. then stirred for over night at r.t. The mixture was quenched with water, then diluted with ether. The organic layer was then washed with $H_2O$, brine, dried over MgSO4, filtered then evaporated. The residue was purified by a flash chromatography (5% AcOEt/Hex) (4.40 g, 78%).

$^1$H NMR (CDCl3). 7.12 (1H, d, J=8.0 Hz), 6.78 (2H, m), 3.84 (3H, s), 2.97 (2H, t, J=6.0 Hz), 2.6 (2H, t, J=6.0 Hz), 2.10 (2H, m), 1.71 (2H, m), 0.63 (6H, t, J=7.5 Hz).

Step 2: 1,1-Diethyl-7-methoxy-3,4-dihydro-1H-naphthalen-2-one oxime (B)

1,1-Diethyl-7-methoxy-3,4-dihydro-1H-naphthalen-2-one (4.40 g, 18.96 mmol) in dry pyridine (20 mL) with the hydroxylamine hydrochloride salt (10.54 g, 151.7 mmol) was heated to 80° C. for one day. The mixture was cooled down to r.t., then the pyridine was removed under vaccum. The green gum was dissolved with AcOEt, washed with $H_2O$, HCl 10%, $H_2O$, brine, dried over MgSO$_4$ and filtered through a small silica pad. The crude compound was used without any other purification (4.69 g, 100%).

1H NMR(CDCl3): 7.94 (1H, s), 7.06 (1H, d, J=8 Hz), 6.84 (1H, d, J=2.5 Hz), 6.73 (1H, dd, J=2.5 and 8 Hz), 3.83 (3H, s), 2.802.75 (4H, m), 2.08 (2H, m), 1.85 (2H, m), 0.68 (6H, t, J=7.5 Hz).

Step 3: 7,7-Diethyl-5-methoxy-1a,2,7,7a-tetrahydro-1H-1-aza-cyclopropa[b]naphthalene (C)

To a solution of 1,1-Diethyl-7-methoxy-3,4-dihydro-1H-naphthalen-2-one oxime (4.68 g, 18.96 mmol) in dry THF (100 mL) at 0° C. was added the diethylamine (4.9 mL, 47.4 mmol) and the LAH (95% powder) (2.16 g, 56.9 mmol). The mixture was stirred at 0° C. for min then heated to reflux for 3 h. The gray solution was cooled down to 0° C., quenched with brine and diluted with AcOEt. The organic layer was decanted, washed with $H_2O$ (2×), brine, dried over MgSO$_4$, filtered then evaporated. The residue was purified by a flash chromatography (3% MeOH/CH$_2$Cl$_2$) (3.889 g, 89%).

1H NMR (CDCl3): 6.99 (1H, d, J=8 Hz), 6.76 (2H, m), 3.13 (2H, m), 2.40 (1H, bs), 2.10–2.05 (2H, m), 1.84 (1H, m), 1.62 (4H, m), 1.02 (3H, t, J=7.5 Hz), 0.75 (3H, t, J=7.5 Hz).

Step 4: 7,7-Diethyl-1a,2,7,7a-tetrahydro-1H-1-aza-cyclopropa[b]naphthalen-5-ol(D)

To a solution of 7,7-Diethyl-5-methoxy-1a,2,7,7a-tetrahydro-1H-1-aza-cyclopropa[b]naphthalene (3.889 g, 16.81 mmol) in CH2Cl2 (170 mL) at −78° C. was added the BBr3 (1M in CH$_2$Cl$_2$) (33.6 mL, 33.62 mmol). The mixture was kept at −78° C. for 30 min then to 0° C. for 1.5 h. The mixture was quenched by NaHCO$_3$, diluted with AcOEt. The organic layer was washed with H2O, brine, dried over MgSO4, filtered then evaporated. The residue was purified by a flash chromatography (3%/MeOH/CH2Cl2) (2.917 g, 80%).

1H NMR (CDCl3): 6.93 (1H, d, J=8.0 Hz), 6.68 (1H, d, J=2.5 Hz), 6.64 (1H, dd, J=8 and 2.5 Hz), 3.12 (2H, m), 2.42 (1H, bs), 2.14 (1H, bs), 2.04 (1H, m), 1.82 (1H, m), 1.65 (4H, m), 1.02 (3H, t, J=7.5 Hz), 0.75 (3H, t, J=7.5 Hz).

Step 5: 5-tert-Butoxycarbonyloxy-7,7-diethyl-1 a,2,7,7a-tetrahydro-1-aza cyclopropa[b]naphthalene-1-carboxylic Acid Tert-Butyl Ester (E)

To a solution of 7,7-Diethyl-1a,2,7,7a-tetrahydro-1H-1-aza-cyclopropa[b]naphthalen-5-ol (1.5 g, 6.90 mmol) in CH$_2$Cl$_2$ (30 mL) at r.t was added the (Boc)20 (3.77 g, 17.26 mmol), the triethylamine (3.85 mL, 27.6 mmol) and DMAP (cat). The mixture was stirred at r.t. for over night. The mixture was quenched by NH4Cl, diluted with AcOEt. The organic layer was washed with H2O, brine, dried over MgSO4, filtered then evaporated. The residue was purified by a flash chromatography (5% to 25% AcOEt/Hex) (2.44 g, 84%).

1H NMR (CDCl3): 7.05–6.95 (3H, m), 3.29 (1H, d, J=17 Hz), 3.04 (1H, dd, J=2 Hz and 17 Hz), 2.94 (1H, m), 2.67 (1H, d, J=6.5 Hz), 2.05–1.95 (2H, m), 1.65–1.50 (11H, m), 1.43 (9H, s), 1.11 (3H, t, J=7.5 Hz), 0.72 (3H, t, J=7.5 Hz).

Step 6: Carbonic acid 7-tert-butoxycarbonylamino-trans-6-ethoxy-8,8-diethyl-5,6,7,8-tetrahydro-naphthalen-2-yl ester tert-butyl ester (F)

5-tert-Butoxycarbonyloxy-7,7-diethyl-1a,2,7,7a-tetrahydro-1-aza-cyclopropa[b]naphthalene-1-carboxylic acid tert-butyl ester (224.0 mg, 0.54 mmol) placed under Argon at room temperature was dissolved in anhydrous ethanol (8.0 mL). To this solution was added a catalytic amount of pyridinium p-toluene sulfonate. The reaction mixture was stirred overnight. The next day, the reaction mixture was poured into an aqueous solution of sodium bicarbonate and it was extracted using dichloromethane. The combined organic layers were dried over sodium sulfate, filtered, and the solvent was removed. The crude was purified by flash chromatography using; hexanes:ethyl acetate (9:1) then (8:2) as the eluent. The isolated product is a solid (129 mg, 55%).

Step 7: Carbonic Acid 7-tert-butoxycarbonylamino-trans-6-ethoxy-8,8-diethyl-5,6,7,8-tetrahydro-naphthalen-2-yl ester tert-butyl ester 5-tert-Butoxycarbonyloxy-7,7-diethyl-1a,2,7,7a-tetrahydro 1-aza-cyclopropa[b]naphthalene-1-carboxylic acid tert-butyl ester (346.0 mg; 0.83 mmol) placed under Nitrogen was dissolved using anhydrous chloroform (15.0 mL) followed by 0.5 equivalents of Ytterbium trifluoromethanesulfonate (257.0 mg; 0.42 mmol) were then added. The reaction mixture was allowed to stir at room temperature overnight. The next day, it was poured into an aqueous solution of sodium bicarbonate and extracted using dichloromethane. The combined organic layers were dried over magnesium sulfate, filtered, and the solvent was removed by vacuo. The crude was purified by flash chromatography using; hexanes:ethyl acetate (9:1) then (8:2) as the eluent. The isolated product is a solid (275 mg, 71%).

1H NMR (400 MHz) (CDCl3; d; ppm): 7.06 (1H, d, J=8.3 Hz), 6.93–6.99 (2H, m). 4.33 (1H, d, J=10.4 Hz); 4.06 (1H, dd, J1=J2=10.0 Hz); 3.72 (1H, m); 3.64 (1H, m); 3.54 (1H, m), 3.22 (1H, dd, J1=6.0 Hz, J2=16.2 Hz), 2.79 (1H, dd, J1=9.5 Hz, J2=16.0 Hz), 1.72 (3H, m), 1.51 (1H, m), 1.55 (9H, s), 1.47 (9H, s), 1.22 (3H, t, J=7.0 Hz); 0.74 (3H, t, J=7.5 Hz); 0.69 (3H, t, J=7.3 Hz).

Step 8: Trans-3-Ethoxy-1,1-diethyl-7-hydroxy-1,2,3,4-tetrahydro-naphthalen-2-yl-ammonium chloride (compound #1)

Carbonic acid 7-tert-butoxycarbonylamino-trans-6-ethoxy-8,8-diethyl-5,6,7,8-tetrahydro-naphthalen-2-yl ester tert-butyl ester (200 mg; 0.43 mmol) placed under nitrogen at room temperature was dissolved in tetrahydrofuran (5.0 mL) and trifluoroacetic acid (3.0 mL) was then added and the reaction mixture was stirred for about an hour. The solvents were then evaporated by vacuo and a solution of hydrochloric acid in ether (1.0M) (50 mL) was then added. The reaction mixture thus obtained was then stirred for another hour. The solvents were removed by vacuo and the isolated solid washed several times with ether than dichloromethane. The isolated product is a yellow powder (145 mg, >99%).

1H NMR (400 MHz) (CD3OD; d; ppm): 6.98 (1H, d, J=8.9 Hz), 6.68 (2H, m). 3.96 (1H, m), 3.87 (1H, m), 3.56 (1H, m), 3.39 (2H, m), 2.57 (1H, dd, J1=10.0 Hz, J2=15.5 Hz), 2.07 (1H, m), 1.73 (1H, m), 1.66 (2H, m), 1.30 (3H, t, J=7.0 Hz) 0.80 (3H, t, J=7.4 Hz), 0.70 (3H, t, J=7.3 Hz).

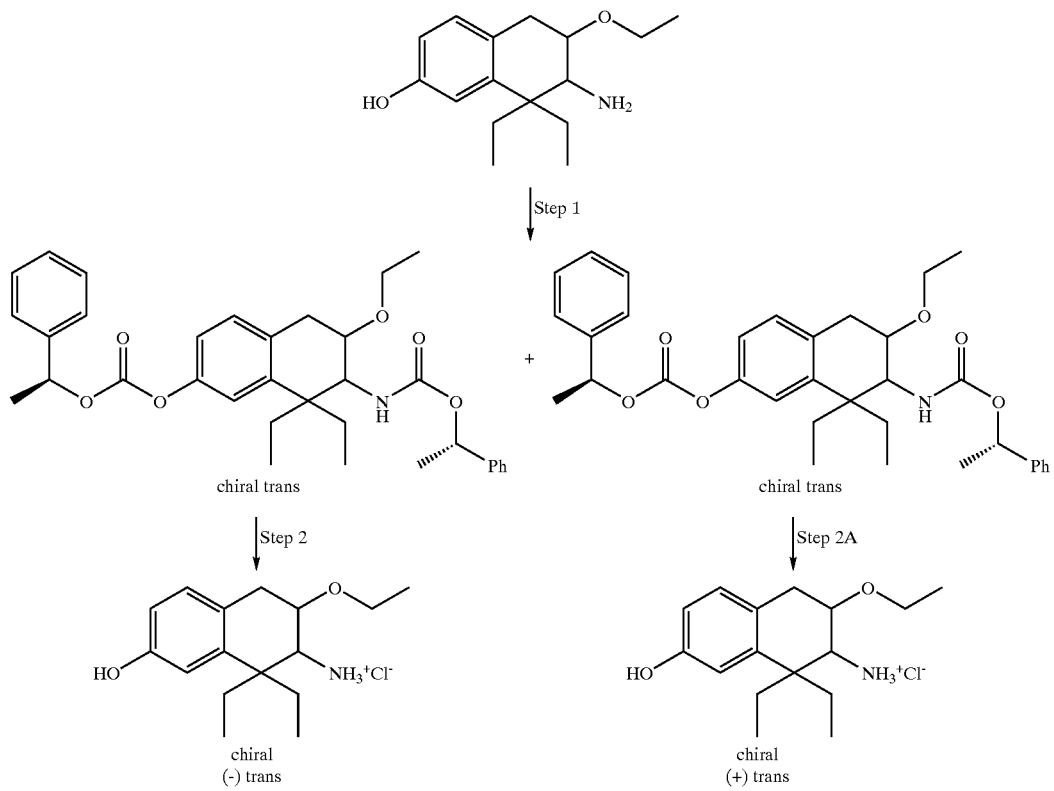

Step 1

Trans-7-Amino-6-ethoxy-8,8-diethyl-5,6,7,8-tetrahydro-naphthalen-2-ol (231 mg; 0.88 mmol) is placed under nitrogen at room temperature and dissolved with anhydrous acetonitrile (20 mL). Triethylamine 0.25 mL (1.75 mmol) and the chiral auxiliary reagent 504 mg (1.75 mmol) are then added. The reaction mixture thus obtained was heated overnight at reflux. The following day, the reaction mixture is cooled back to room temperature and it is then poured into an aqueous solution of sodium bicarbonate and extracted using dichloromethane. The combined organic layers were washed with 0.1N. HCl, brine, and were then dried over sodium sulfate. After filtration, the solvent was removed by vacuo. The crude was purified by flash chromatography using; hexanes; ethyl acetate (9:1) then (8:2) as the eluent. The isolated products are a colorless oils (72%).

(less polar isomer): 1H NMR (400 MHz) (CDCl3; d; ppm): 7.41 (10H, m); 7.03 (1H, m); 6.94 (2H, m); 5.84 (2H, m); 4.54 (1H, d); 4.10 (1H, m); 3.61 (2H, m); 3.39 (1H, m); 3.19 (1H, m); 2.72 (1H, m); 1.71 (2H, m); 1.64 (3H, d); 1.50–1.62 (2H, m); 1.57 (3H, d) 0.98 (3H, t, J=7.0 Hz); 0.72 (6H, 2t).

(more polar isomer): 1H NMR (400 MHz) (CDCl3; d; ppm): 7.37 (10H, m); 7.03 (1H, m) 6.95 (2H, m); 5.82 (2H, m); 4.51 (1H, d); 4.10 (1H, m); 3.71 (2H, m); 3.55 (1H, m); 3.23 (1H, dd); 2.80 (1H, dd); 1.40–1.78 (4H, m); 1.67 (3H, d); 1.56 (3H, d) 1.22 (3H, t); 0.68 (6H, 2t).

Step 2

(−)Trans-3-Ethoxy-1,1-diethyl-7-hydroxy-1,2,3,4-tetrahydro-naphthalen-2-yl-ammonium chloride (compound #16)

Carbonic acid trans-6-ethoxy-8,8-diethyl-7-(1-phenyl-ethoxycarbonylamino-5,6,7,8-tetrahydro-naphthalen-2-yl ester 1-phenyl-ethyl ester (less polar isomer) (31 mg; 0.055 mmol) placed under nitrogen at room temperature was dissolved in dichloromethane (8.0 mL) and trifluoroacetic acid (3.0 mL) was then added and the reaction mixture was stirred for about an hour. The solvents were then evaporated by vacuo and a solution of hydrochloric acid in ether (11.0M) (7 mL) was then added. The reaction mixture thus obtained was then stirred for another hour. The solvents were removed by vacuo and the isolated solid washed several times with ether, hexanes, than dichloromethane. The isolated product is a yellow powder (15.7 mg, 95%).

1H NMR (400 MHz) (CD3OD; d; ppm): 6.98 (1H, d, J=8.9 Hz, aromatic), 6.68 (2H, m, aromatics). 3.96 (1H, m, CH—NH2), 3.87 (1H, m), 3.56 (1H, m), 3.39 (2H, m), 2.57 (1H, dd, J1=; 10.0 Hz, J2=15.5 Hz), 2.07 (1H, m), 1.73 (1H, m), 1.66 (2H, m), 1.30 (3H, t, J=7.0 Hz) 0.80 (3H, t, J=7.4 Hz), 0.70 (3H, t, J=7.3 Hz). [α]D +43.00 c=0.2

Step 2A (+)Trans-3-Ethoxy-1,1-diethyl-7-hydroxy-1,2,3,4-tetrahydro-naphthalen-2-yl-ammonium chloride (compound #16)

Carbonic acid trans-4-ethoxy-8,8-diethyl-7-(1-phenyl-ethoxycarbonylamino)-5,6,7,8-tetrahydro-naphthalen-2-yl ester 1-phenyl-ethyl ester (more polar isomer) (32 mg, 0.057 mmol) placed under nitrogen at room temperature was dissolved in dichloromethane (5.0 mL) and trifluoroacetic acid (3.0 mL) was then added and the reaction mixture was stirred for about an hour. The solvents were then evaporated by vacuo and a solution of hydrochloric acid in ether (1.0M) (10 mL) was then added. The reaction mixture thus obtained was then stirred for another hour. The solvents were removed by vacuo and the isolated solid washed several times with pentane, hexanes, than dichloromethane. The isolated product is a yellow powder (10.3 mg, 60%).

1H NMR (400 MHz) (CD3OD; d; ppm): 6.98 (1H, d, J=8.9 Hz, aromatic), 6.68 (2H; m). 3.96 (1H, m), 3.87 (1H, m), 3.56 (1H, m), 3.39 (2H, m), 2.57 (1H, dd, J1=10.0 Hz, J2=150.5 Hz), 2.07 (1H, m, CH2), 1.73 (1H, m), 1.66 (2H, m), 1.30 (3H, t, J=7.0 Hz) 0.80 (3H, t, J=7.4 Hz), 0.70 (3H, t, J=7.3 Hz). [α]D −43.68 c=0.19.

In a like manner, the following compounds were prepared:

Compound #2

(±)-TRANS-7-AMINO-METHOXY-8,8-DIMETHYL-5,6,7,8 TETRAHYDRO-NAPHTHALEN-2-OL HCL SALT

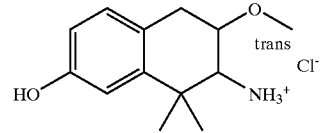

1H NMR (400 MHz) (DMSO-d6; d; ppm): 9.24 (1H, bs), 8.30 (3H, bs), 6.88 (1H, d, J=9.3 Hz), 6.74 (1H, d. J=2.2 Hz), 6.59 (1H, dd, J=2.2 and 9.3 Hz), 3.65 (1H, m), 3.43 (3H, s), 3.40 (1H, m), 3.27 (1H, m), 3.13 (1H, m), 1.40 (3H, s), 1.17 (3H, s).

Compound #3

(±)-TRANS-7-AMINO-8,8-DIMETHYL-6-PHENOXY-5,6,7,8-TETRAHYDRO-NAPHTHALEN-2-OL TFA SALT

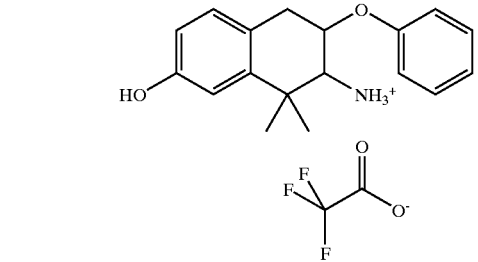

1H NMR (400 MHz) (DMSO-d6; d; ppm): 9.26 (1H, bs), 8.31 (3H, bs), 7.34 (2H; t, J=8.5 Hz), 7.15 (2H, d, J=8.1 Hz), 7.01 (1H, t, J=7.2 Hz), 6.88 (1H, d, J=8.4 Hz), 6.78 (1H, d, J=2.4 Hz), 6.60 (1H, dd, J=2.4 and 8.4 Hz), 4.74 (1H,m), 3.51 (1H, m), 3.30 (1H, dd, J=5.4 and 10.3 Hz), 2.72 (1H, dd, J=4 and 10.3 Hz), 1.47 (3H, s), 1.24 (3H, s).

Compound #4

1,1-DIETHYL-7-HYDROXY-TRANS-3-ISOPROPOXY-1,2,3,4-TETRAHYDRO-NAPHTHALEN-2-YL-AMMONIUM CHLORIDE

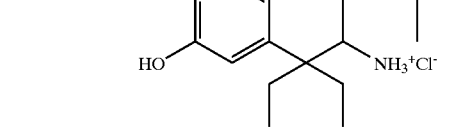

1H NMR (400 MHz) (CD3OD; d; ppm): 6.98 (1H, d, J=9.0 Hz), 6.67 (2H, m). 4.04 (1H, m), 3.97 (1H, m), 3.34 (1H, m), 3.32 (1H, m), 2.58 (1H, dd, J1=10.0 Hz, J2=15.6 Hz), 2.05 (1H, m), 1.76 (1H, m), 1.68 (2H, dd, J1=7.5 Hz, J2=15.1 Hz), 1.28 (3H, d, J=6.1 Hz), 1.25 (3H, d, J=6.0 Hz), 0.79 (3H,t, J=7.5 Hz), 0.69 (3H, t, J=7.2 Hz).

Compound #5

(±)1,1-DIETHYL-7-HYDROXY-TRANS-3-PROPOXY-1,2,3,4-TETRAHYDRO-NAPHTHALEN-2-YL-AMMONIUM CHLORIDE

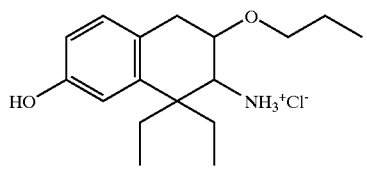

1H NMR (400 MHz) (CD3OD; d; ppm): 6.97 (1H, d, J=8.7 Hz), 6.66 (2H, m). 3.94 (1H, m), 3.72 (1H, m), 3.48 (1H, dd, J1=7.0 Hz, J2=14.1 Hz), 3.39 (1H, m), 3.37 (1H, m), 2.55 (1H, dd, J1—9.8 Hz, J2=15.3 Hz), 2.06 (1H, m), 1.67 (5H, m), 1.00 (3H, t, J=7.3 Hz), 0.78 (3H, t, J=7.3 Hz), 0.68 (3H, t, J=7.0 Hz).

Compound #6
(±)1,1-DIETHYL-7-HYDROXY-TRANS-32-PHENOXY-ETHOXY) 1,2,3,4-TETRAHYDRO-NAPHTHALEN-2-YL-AMMONIUM CHLORIDE

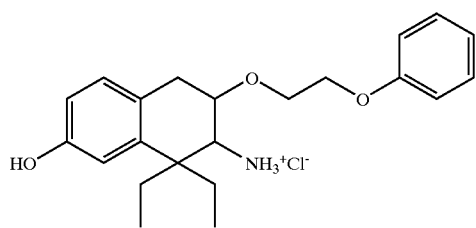

1H NMR (400 MHz) (CD3OD; d; ppm): 7.29 (2H, m), 6.96 (4H, m), 6.69 (2H, m), 4.23 (2H, m), 4.13 (2H, m), 3.93 (1H, m), 3.45 (2H, m), 2.64 (1H, dd, J1=9.9 Hz, 12=15.5 Hz), 2.07 (1H, m), 1.72 (1H, m), 1.67 (2H, m), 0.80 (3H, t, J=7.5 Hz), 0.70 (3H, t, J=7.2 Hz).

(±) Compound #7
7-AMINO-TRANS-6-ETHOXY-8,8-DIMETHYL-5,6,7,8-TETRAHYDRO-NAPHTHALEN-2-OL HCL SALT

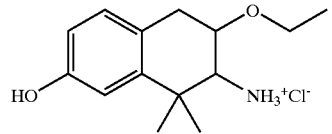

1H NMR (400 MHz) (CD3OD; d; ppm): 6.94 (1H, d, J=8.3 Hz), 6.79 (1H, d, 1=2.4 Hz). 6.64 (1H, dd, J1=2.4 Hz, J2=8.3 Hz), 3.87 (1H, m), 3.77 (1H, m), 3.56 (1H, m), 3.35 (1H, m), 3.23 (1H, dd, J1=Hz, J2=10.8 Hz), 2.63 (1H, dd, J1=10.4 Hz, J2=15.3 Hz), 1.49 (3H, s), 1.31 (3H, t, J=7.0 Hz), 1.25 (3H, s).

Compound #8
(±)1,1-DIETHYL-7-HYDROXY-TRANS-3-(2-METHOXY-ETHOXY)-1,2,3,4-TETRAHYDRO-NAPHTHALEN-2-YL-AMMONIUM CHLORIDE

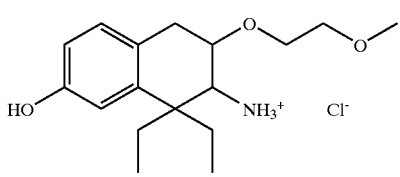

1H NMR (400 MHz) (DMSO-d6; d; ppm): 9.24 (1H, bs), 7.97 (3H, bs), 6.91 (1H, d, J=8.2 Hz), 6.60 (2H, m), 3.89 (1H, m), 3.79 (1H, m), 3.66 (1H, m), 3.54 (2H, m), 3.45 (2H, m), 3.28 (3H, s), 3.20 (1H, m), 1.84 (2H, m), 1.35 (2H,m), 0.66 (3H, t, J=7.3 Hz), 0.56 (3H, t, J=7.1 Hz).

Compound #9 (*)1,1-DIE 7-HYDROXY-TRANS-3-METHOXY-1,2,3,4 TETRAHYDRO-NAPHTHALEN-2-YL-AMMONIUM CHLORIDE

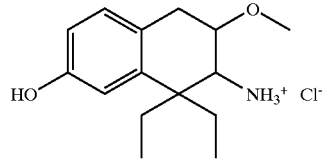

1H NMR (400 MHz) (CD3OD; d; ppm): 7.00 (1H, d, J=6,4 Hz), 6.68 (2H, m). 3.87 (1H, m), 3.53 (3H, s), 3.41 (2H, m), 2.54 (1H, dd, J1=10 Hz, J2=16 Hz), 2.07 (1H, m), 1.71 (1H, m), 1.66 (2H, m), 0.80 (3H, t, J=7.5H), 0.70 (3H, t, J=7.3 Hz).

Compound #10
(±)1,1-DIETHYL-7-HYDROXY-TRANS-3-(2-HYDROXY-ETHOXY)-1,2,3,4-TETRAHYDRO-NAPHTHALEN-2-YL-AMMONIUM CHLORIDE 1H NMR (400 MHz) (DMSO-d6; d; ppm): 9.22 (1H, bs), 7.96 (3H, bs), 6.91 (1H, d, J=8.2 Hz), 6.60 (2H, m), 4.70 (1H,bs), 3.89 (1H, m), 3.79 (1H, m), 3.66 (1H, m), 3.54 (2H, m), 3.45 (2H, m), 3.20 (1H, m), 1.83 (2H, m), 1.58 (2H,m), 0.66 (3H, t, J=7.3 Hz), 0.57 (3H, t, J=7.1 Hz).

Compound #11
(±)-1,1-spiropentanyl trans-7-hydroxy-3-methoxy-1,2,3,4-tetrahydro-naphthalen-2-yl-ammonium; trifluoro-acetate 1H NMR (MeOD): 6.95 (1H, d, J=8.5 Hz), 6.73 (1H, d, J=2.5 Hz), 6.63 (1H, dd. 3=2.5 Hz and 8.5 Hz), 3.66 (1H, m), 3.53 (3H, s), 3.45–3.35 (2H, m), 2.65 (1H, dd, J=10 Hz and 16 Hz), 2.20 (1H, m), 2.15–1.95 (5H, m), 1.80–1.65 (2H,m).

Compound #12
(±)7-Hydroxy-3-methoxy-1,1-dipropyl-1,2,3,4-tetrahydro-naphthalen-2-yl-ammonium; trifluoro-acetate 1H NMR (MeOD): 6.99 (1H, d, J=8.0 Hz), 6.70–6.65 (2H, m), 3.84 (1H, qd, J=6.0 hz and 10.0 Hz), 3.53 (3H, s), 3.45–3.35 (2H, m), 2.54 (1H, dd, J=10.0 Hz and 15.5 Hz), 1.95 (1H, m), 1.73 (1H, m), 1.65–1.45 (2H, m), 1.30–1.05 (3H, m), 0.95–0.90 (4H, m), 0.86 (3H, t, J=7.0 Hz).

Compound #13
(±)3-Ethoxy-7-hydroxy-1,1-dipropyl-1,2,3,4-tetrahydro-naphthalen-2-yl-ammonium; trifluoro-acetate

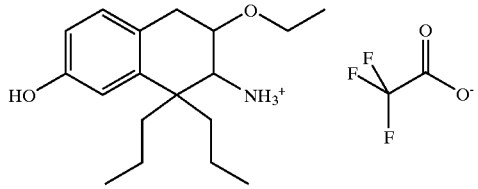

1H NMR (MeOD): 6.98 (1H, d, J=8.0 Hz), 6.70–6.65 (2H, m), 4.00–3.85 (2H, m), 3.57 (1H, m), 3.39 (2H, m), 2.57 (1H, dd, J=10.0 Hz and 15.5 Hz), 1.95 (1H, m), 1.77 (1H, m), 1.65–1.50 (2H, m), 1.31 (3H, t, J=7.0 Hz), 1.30–1.05 (3H, m), 0.95–0.90 (4H, m), 0.86 (3H, t, J=7.0 Hz).

Compound #14
(*)7-Hydroxy-3 (2-phenoxy-ethoxy)-1,1-dipropyl-1,2,3,4-tetrahydro-naphthalen-2-yl-ammonium; trifluoro-acetate

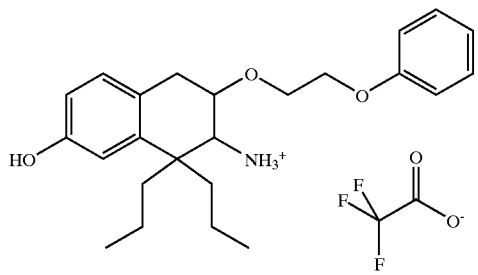

1H NM (MeOD): 7.31 (2H, t, J=8.0 Hz), 7.05–6.95 (4H, m), 6.70–6.65 (2H, m), 4.25 (2H, t, J=5.0 Hz), 4.20–4.05 (2H, m), 3.95 (1H, m), 3.50–3.45 (2H, m), 2.64 (1H, dd, J=10.0 Hz and 15.5 Hz), 1.95 (1H, m), 1.80–1.50 (3H, m), 1.30–1.05 (4H, m), 0.95–0.90 (4H, m), 0.86 (3H, t, J=7.0 Hz).

Compound #15

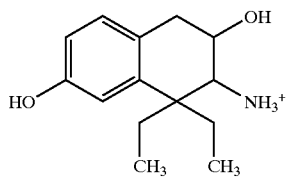

Compound #16
(−)Trans-3-Ethoxy-1,1-diethyl-7-hydroxy-1,2,3,4-tetrahydro-naphthalen-2-yl-ammonium chloride

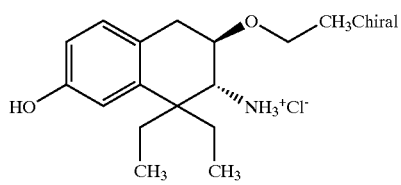

Compound #17
(+)Trans-3-Ethoxy-1,1-diethyl-7-hydroxy-1,2,3,4-tetrahydro-naphthalen-2-yl ammonium chloride

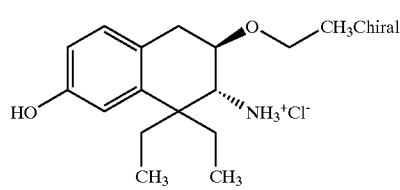

Compound #18
1,1-diethyl-7-hydroxy-3-trans(3-hydroxy-propoxy)-1,2,3,4-tetrahydro-naphthalen-2-yl-ammonium; chloride

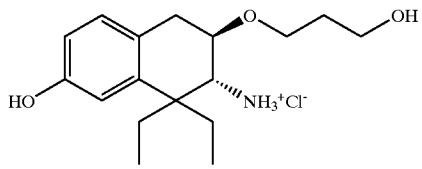

NMR (¹H, DMSO): 9.22(bs, 1H), 7.96 (s, 3H), 6.91(m, 1H), 6.59 (m, 2H), 4.65 (m, 1H), 4.00–3.00 (m, 8H), 2.10–1.70 (m, 4H), 1.54 (m, 2H), 0.66 (t, J=7.2 Hz, 3H), 0.57 (t, J=6.9 Hz, 3H).

Compound #19
7-Amino-6-(2-amino-ethoxy)-8,8-diethyl-5,6,7,8-tetrahydro-naphthalen-2-ol; BIS-trifluoroacetic acid salt

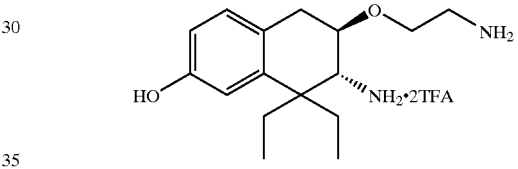

¹H NMR (DMSO): 9.28 (1H, s), 7.91 (3H, broad), 7.80 (3H, broad), 6.93 (1H, d, J=8.5 Hz), 6.64 (2H, m), 4.00–3.90 (2H, m), 3.60 (1H, m), 3.30 (2H, m), 3.20–3.05 (2H, m), 1.92 (1H, m), 1.84 (1H, m), 1.61 (2H, m), 0.69 (3H, t, J=7.5 Hz), 0.59 (3H, t, J=7.5 Hz).

Compound #20
3-(3-Amino-4,4-diethyl-6-hydroxy-1,2,3,4-tetrahydro-naphthalen-2-yloxy)-propionic acid; trifluoroacetic acid salt

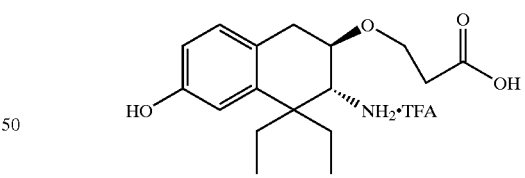

NMR (¹H, DMSO): 9.25 (bs, 1H), 7.87 (s, 3H), 6.93 (m,1H), 6.60 (m, 2H), 3.90 (m, 2H), 3.71 (m, 2H), 3.30(m, 1H), 3.20 (m, 1H), 2.60 (m, 2H), 2.48 (m, 1H), 1.88 (m, 1H), 1.77 (m, 1H), 1.54 (en 2H), 0.67 (t, J=7.2 Hz, 3H), 0.58 (t, J=6.9 Hz, 3H).

Biological Assays

A. Receptor Affinity—Radioligand Binding Assay

Affinity for μ and δ opioid receptors was assessed in vitro using radioligand binding assay employing rat brain membrane preparations as described in Schiller et al., Biophys. Res. Commun., 85, p.1322 (1975) incorporated herein by reference. Male Sprague-Dawley rats weighing between 350–450 g were sacrificed by inhalation of $CO_2$. The rats were decapitated and the brains minus cerebellum were removed and place in ice-cold saline solution and then homogenized in ice-cold 50 mM Tris buffer pH 7.4 (10 ml/brain). The membranes were centrifuged at 14000 rpm for 30 min. at 4° C. The pellets were re-suspended in approximately 6 ml/brain of ice-cold Tris buffer 50 mM pH 7.4 and stored at −78° C. until ready for use. Protein quantification of the brain homogenate was conducted according to protein assay kit purchased (Bio-Rad).

(3H)-DAMGO and (311) DAGLE were used as radioligands for the μ and δ receptors, respectively. Radioligand 50 μl, membranes 100 μl and serially diluted test compound were incubated for 1 hr at 22° C. Non specific binding was determined using 500 fold excess of unlabeled ligand in the presence of tracer and membranes. Free ligand was separated from bound by filtration through Whatman GF/B paper (presoaked in polyethylenimine 1% aqueous solution) and rinsing with ice-cold 50 mM Tris pH 7.4 using a Brandel cell harvester. The filters were dried and radioactivity was counted in a 24 well microplate in the presence of 500 ml scintillant per well. Radioactivity was measured using a Wallac 1450 Microbeta counter. Inhibition constants (Ki) for the various compounds were determined from the IC50 according to the Cheng and Prusoff equation.

B. Central and Peripheral Analgesia—PBQ Writhing Assay

PBQ (phenyl-p-benzoquinone) induced writhing in mice was used to assess both central and peripheral analgesia of compounds of the invention according to the experimental protocol described in Sigmund et al., Proc. Soc. Exp. Biol. Med., 95, p. 729(1957) which is incorporated herein by reference. The test was performed on CD #1 male mice weighing between 18 and 22 g. The mice were weighed and marked and administered peritoneally with 0.3 ml/20 g by weight 0.02% solution of phenylbenzoquinone (PBQ). The contortions which appeared during a 15 minute time period following the injection were counted and ED50 values (dose of compound which induced a 50% reduction in the number of writhes observed compared to the control) was calculated. The PBQ was injected at time intervals of 5, 20 or 60 minutes after subcutaneous or oral administration of the compound (or medium, or standard).

PBQ solution was prepared by dissolving 20 mg of PBQ in 5 ml ethanol 90% (sigma, reagent, alcohol). The dissolved PBQ was slowly added to 95 ml of distilled water continuously shaken and preheated (not boiled). The PBQ solution was left 2 hours before use, and at all times, protected from light A new solution was prepared every day for the test.

C. Central Analgesia Tail Flick Assay

The compounds of the present invention were evaluated for central analgesia as described in D'Amour et al. J. Pharmacol. 72:74–79, 1941 which is herein incorporated by reference.

The results are shown on Table 1

TABLE 1

| Compound # | $Ki_u$ |
|---|---|
| #1 | 0.5 |
| #2 | 1.6 |
| #3 | 29.5 |
| #4 | 1.9 |
| #5 | 1.2 |
| #6 | 0.43 |
| #7 | 23.7 |
| #8 | 15 |
| #9 | 0.24 |
| #10 | 3.6 |
| #11 | 87.2 |
| #12 | 2.6 |

TABLE 1-continued

| Compound # | $Ki_u$ |
|---|---|
| #13 | 45.6 |
| #14 | 63 |
| #15 | 1.2 |
| BCH-14330 | 0.41 |
| BCH-14501 | 1.4 |
| #18 | 2.88 |
| BCH15149 | |
| #19 | 7.4 |
| BCH-15182 | |
| #20 | 23.8 |
| BCH-15183 | |

While the invention has been described in connection with specific embodiments thereof, it will be understood that it is capable of further modifications and this application is intended to cover any variations, uses or adaptations of the invention following, in general, the principles of the invention and including such departures from the present description as come within known or customary practice within the art to which the invention pertains, and, as may be applied to the essential features hereinbefore set forth, and as follows in the scope of the appended claims.

What is claimed is:

1. A compound represented by formula (I)

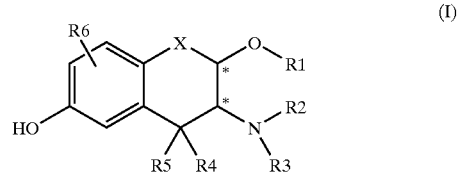

and pharmaceutically acceptable derivatives thereof; wherein;

X is selected from any one of
(i) a bond;
(ii) —$CR_7R_8$— wherein $R_7$ and $R_8$ are independently selected from the group consisting of H, OH, halogen, CN, COOH, $CONH_2$, amino, nitro, SH, $C_{1-6}$ alkyl wherein one or more of the carbon atoms may optionally be substituted by one or more heteroatoms selected from O, S and N, $C_{1-6}$ alkenyl where one or more of the carbon atoms may optionally be substituted by one or more heteroatoms selected from O, S and N, $C_{2-6}$ alkynyl where one or more of the carbon atoms may optionally be substituted by one or more heteroatoms selected from O, S and N; and $COOR_c$ wherein $R_c$ is $C_{1-6}$ alkyl, $C_{2-6}$ alkenyl or $C_{2-6}$ alkynyl; $R_7$ and $R_8$ can also be connected to form a $C_{3-8}$ cycloalkyl, a $C_{3-8}$ cycloalkenyl or a saturated heterocycle of from 3 to 8 atoms;

$R_1$ is selected from the group consisting of H, $C_{1-12}$ alkyl where one or more of the carbon atoms may optionally be substituted by one or more heteroatoms selected from O, S and N, $C_{2-12}$ alkenyl where one or more of the carbon atoms may optionally be substituted by one or more heteroatoms selected from O, S and N, $C_{2-12}$ alkynyl where one or more of the carbon atoms may optionally be substituted by one or more heteroatoms selected from O, S and N, $C_{6-12}$ aryl, $C_{6-12}$ aralkyl, $C_{6-12}$ aryloxy, $C_{1-12}$ acyl, heteroaryl having from 6 to 12 atoms, and phosphoryl;

R₂ and R₃ are independently selected from the group consisting of $C_{1-6}$ alkyl where one or more of the carbon atoms may optionally be substituted by one or more heteroatoms selected from O, S and N, $C_{2-6}$ alkenyl where one or more of the carbon atoms may optionally be substituted by one or more heteroatoms selected from O, S and N, $C_{2-6}$ alkynyl where one or more of the carbon atoms may optionally be substituted by one or more heteroatoms selected from O, S and N, $C_{6-12}$ aryl, $C_{6-12}$ aralkyl, heteroaryl having from 6 to 12 atoms, and H; or R₂ and R₃ may together form a saturated heterocycle of from 3 to 8 atoms;

R₄ and R₅ are independently selected from the group consisting of $C_{1-6}$ alkyl where one or more of the carbon atoms may optionally be substituted by one or more heteroatoms selected from O, S and N, $C_{2-6}$ alkenyl where one or more of the carbon atoms may optionally be substituted by one or more heteroatoms selected from O, S and N, $C_{2-6}$ alkynyl where one or more of the carbon atoms may optionally be substituted by one or more heteroatoms selected from O, S and N, and H;

R₄ and R₅ can also be connected to form $C_{3-8}$ cycloalkyl, a $C_{3-8}$ cycloalkenyl or a saturated heterocycle of from 3 to 8 atoms;

R₆ is hydrogen, OH, $C_{1-6}$ alkyl where one or more of the carbon atoms may optionally be substituted by one or more heteroatoms selected from O, S and N, $C_{2-6}$ alkenyl where one or more of the carbon atoms may optionally be substituted by one or more heteroatoms selected from O, S and N, $C_{2-6}$ alkynyl where one or more of the carbon atoms may optionally be substituted by one or more heteroatoms selected from O, S and N, O—$C_{1-6}$ alkyl where one or more of the carbon atoms may optionally be substituted by one or more heteroatoms selected from O, S and N, O—$C_{2-6}$ alkenyl where one or more of the carbon atoms may optionally be substituted by one or more heteroatoms selected from O, S and N, O—$C_{2-6}$ alkynyl where one or more of the carbon atoms may optionally be substituted by one or more heteroatoms selected from O, S and N, halogen, CN, COOH, CONH₂, amino, nitro, or SH;

with the provisos that:
1) nt both R₄ and R₅ are not both H; and
2) at least one of R₂ and R₃ is H or $C_{1-6}$ alkyl.

2. The compound of claim 1 wherein X is —CH₂—.

3. The compound of claim 2 wherein the geometric relation between the substituents of carbons marked by an * is trans.

4. The compound of claim 3 wherein R₂ and R₃ are H.

5. The compound of claim 3 wherein R₆ is H.

6. The compound of claim 5 wherein R₄ and R₅ are $C_{1-6}$ alkyl.

7. The compound of claim 5 wherein R₄ and R₅ are independently selected from the group consisting of methyl, ethyl, isopropyl, propyl, butyl, and isobutyl.

8. The compound of claim 5 wherein R₄ and R₅ are ethyl.

9. The compound of claim 5 wherein R₄ and R₅ are methyl.

10. The compound of claim 5 wherein R₁ is selected from the group consisting of H, $C_{1-12}$ alkyl, $C_{6-12}$ aryl, and $C_{6-12}$ aralkyl.

11. The compound of claim 5, wherein R₁ is selected from the group consisting of $C_{1-6}$ alkyl, $C_{6-12}$ aryl, and $C_{6-12}$ aralkyl.

12. The compound of claim 5 wherein R₁ is $C_{1-6}$ alkyl.

13. The compound of claim 5 wherein R₁ is selected from the group consisting of CH₃, —(CH₂)ₙ—CH₃, and —(CH₂)ₙ—OCH₃ wherein n is an integer selected between 1 and 5.

14. The compound of claim 5 wherein R₁ is $C_{6-12}$ aryl.

15. The compound of claim 14 wherein R₁ is selected from the group consisting of

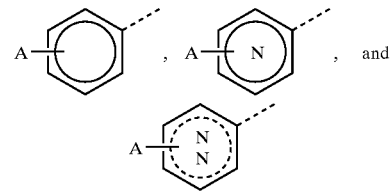

wherein A is selected from the group consisting of $C_{1-6}$ alkyl, $C_{1-6}$ alkyl, $C_{2-6}$ alkenyl, $C_{2-6}$ alkynyl, O—$C_{2-6}$ alkenyl, O—$C_{2-6}$ alkynyl, S—$C_{1-6}$ alkyl, S—$C_{2-6}$ alkenyl, S—$C_{2-6}$ alkynyl, N—$C_{1-6}$ alky, N—$C_{2-6}$ alkenyl, N—$C_{2-6}$ alkynyl, CF₃, fluoro, chloro, bromo, iodo, OH, SH, CN, nitro, ammo, aminoamidino, amidino, guanido, COOH, and COOR$_x$ wherein R$_x$ is $C_{1-6}$ alkyl, $C_{2-6}$ alkenyl, or $C_{2-6}$ alkynyl.

16. The compound of claim 5 wherein R₁ is $C_{6-12}$ aralkyl.

17. The compound of claim 16, wherein R₁ is selected from the group consisting of

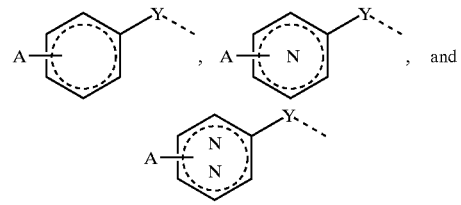

wherein A is selected from the group consisting of $C_{1-6}$ alkyl, $C_{1-6}$ alkyl, $C_{2-6}$ alkenyl, $C_{2-6}$ alkynyl, O—$C_{1-6}$ alkyl, O—$C_{2-6}$ alkenyl, O—$C_{2-6}$ alkynyl, S—$C_{1-6}$ alkyl, S—$C_{2-6}$ alkenyl, S—$C_{2-6}$ alkynyl, N—$C_{2-6}$ alkyl, N—$C_{2-6}$ alkenyl, N—$C_{2-6}$ alkynyl, CF₃, fluoro, chloro, bromo, iodo, OH, SH, CN, nitro, amino, aminoamidino, amidino, guanido, COOH, and COOR$_z$ wherein R$_z$ is $C_{1-6}$ alkyl, $C_{2-6}$ alkenyl, or $C_{2-6}$ alkynyl and Y is —(CH₂)$_m$— wherein m is an integer selected between 1 and 5.

18. The A compound selected from the group consisting of:

Trans-7-Amino-6-ethoxy-8,8-diethyl-5,6,7,8-tetrahydro-naphthalen-2-ol (compound #1);
Trans-7-Amino-6-methoxy-8,8-dimethyl-5,6,7,8-tetrahydro-naphthalen-2-ol (compound #2);
Trans-7-Amino-8,8-dimethylphenoxy-5,6,7,8-tetrahydro-naphthalen-2-ol (compound #3);
Trans-7-Amino-6-isopropoxy-8,8-dimethyl-5,6,7,8-tetrahydro-naphthalen-2-ol (compound #4);
Trans-7-Amino-8,8-dimethyl-6-propoxy-5,6,7,8-tetrahydro-naphthalen-2-ol (compound #5);
Trans-7-Amino-8,8-dimethyl-6-(2-phenoxy-ethoxy)5,6,7,8-tetrahydro-naphthalen-2-ol (compound #6);
Trans-7-Amino-6-ethoxy-8,8-dimethyl-5,6,7,8-tetrahydro-naphthalen-2-ol (compound #7);
Trans-7-Amino-8,8-diethyl-6-(2-methoxy-ethoxy)-5,6,7,8-tetrahydro-naphthalen-2-ol (compound #8);
Trans-7-Amino-8,8-diethyl-6-methoxy-5,6,7,8-tetrahydro-naphthalen-2-ol (compound #9);
Trans-7-Amino-8,8-diethyl-6-(2-hydroxy-ethoxy)-5,6,7,8-tetrahydro-naphthalen-2-ol (compound #10);

Trans-7-Amino-8,8-spiropentanyl-6-methoxy-5,6,7,8-tetrahydro-naphthalen-2-ol (compound #11);

Trans-7-Amino-6-methoxy-8,8-dipropyl-5,6,7,8-tetrahydro-naphthalen-2-ol (compound #12);

Trans-7-Amino-6-ethoxy-8,8-dipropyl-5,6,7,8-tetrahydro-naphthalen-2-ol (compound #13);

Trans-7-Amino-6-(2-phenoxy-ethoxy)-8,8-dipropyl-5,6,7,8-tetrahydro-naphthalen-2-ol (compound #14);

Trans-3-Amino-4,4-diethyl-1,2,3,4-tetrahydro-naphthalene-2,6-diol (compound #15);

(−)Trans-3-Ethoxy-1,1-diethyl-7-hydroxy-1,2,3,4-tetrahydro-naphthalen-2-yl-ammonium chloride (compound #16)

(+)Trans-3-Ethoxy-1,1-diethyl-7-hydroxy-1,2,3,4-tetrahydro-naphthalen-2-yl-ammonium chloride (compound #17); 1,1-diethyl-7-hydroxy-3-trans-3-hydroxy-propoxy)-1,2,3,4-tetrahydro-naphthalen-2-yl ammonium chloride (compound #18);

7-Amino-6-(2-amino-ethoxy)-8,8-diethyl-5,6,7,8-tetrahydro-naphthalen-2-ol BIS-trifluoroacetic acid salt (compound # 19);

3-(3-Amino-4,4-diethyl-6-hydroxy-1,2,3,4-tetrahydro-naphthalen-2-yloxy)-propionic acid; trifluoroacetic acid salt (compound #20);

and pharmaceutically acceptable derivatives thereof.

19. The compound of claim 18 wherein said compound selected from the group consisting of compound #1, compound #2, compound #3, compound #4, compound #5, compound #6, compound #7, compound #8, compound #9, compound #12, compound #16, compound #17, compound #18, and compound #19.

20. The compound of claim 19 wherein said compound selected from the group consisting of compound #1, compound #2, compound #5, compound #8, compound #9, compound #16, and compound #17.

21. The compound of claim 19 wherein said compound selected from the group consisting of compound #16, and compound #17.

22. A compound according to any one of claims 1 to 20 wherein said compound is in the form of the (+) enantiomer, the (−) enantiomer and mixture of the (+) and (−) enantiomer including racemic mixture.

23. A compound according to any one of claims 1 to 20 wherein said compound is in the form of the (+) enantiomer.

24. A compound according to any one of claims 1 to 20 wherein said compound is in the form of the (−) enantiomer.

25. A method of treating pain in a mammal comprising administering to said mammal an analgesic amount of a compound as defined in any one of claims 1 to 20.

26. A pharmaceutical composition comprising a compound as defined in any one of claims 1 to 20 and pharmaceutically acceptable carriers, diluents or adjuvants.

27. The compound of any one of claims 1–21, wherein said pharmaceutically acceptable derivatives are pharmaceutically acceptable salts, esters or salts of said esters.

28. The compound of claim 27, wherein said pharmaceutically acceptable derivatives are pharmaceutically acceptable salts.

29. The compound of claim 28, wherein said compound is in the form of the (+) enantiomer.

30. The compound of claim 28, wherein said compound is in the form of the (−) enantiomer.

31. A pharmaceutical composition comprising the compound of claim 28 and a pharmaceutically acceptable carrier, diluent or adjuvant.

32. A method of treating a mammal for pain, comprising administering to said mammal a pharmaceutically effective amount of the compound of claim 28.

* * * * *